United States Patent [19]
Sigurdsson

[11] Patent Number: 6,132,365
[45] Date of Patent: *Oct. 17, 2000

[54] VALVE

[76] Inventor: Per Arne Sigurdsson, Pl. 3020 Årnäs, S-432 96 Åskloster, Sweden

[ * ] Notice: This patent issued on a continued prosecution application filed under 37 CFR 1.53(d), and is subject to the twenty year patent term provisions of 35 U.S.C. 154(a)(2).

[21] Appl. No.: 08/666,454
[22] PCT Filed: Dec. 29, 1994
[86] PCT No.: PCT/SE94/01264
  § 371 Date: Jun. 27, 1996
  § 102(e) Date: Jun. 27, 1996
[87] PCT Pub. No.: WO95/17862
  PCT Pub. Date: Jul. 6, 1995

[30] Foreign Application Priority Data

Dec. 30, 1993 [SE] Sweden ................................. 9304372

[51] Int. Cl.[7] .................................................. A61M 21/00
[52] U.S. Cl. .................................................. 600/29; 600/30
[58] Field of Search .......................................... 600/29–32

[56] References Cited

U.S. PATENT DOCUMENTS

| | | | |
|---|---|---|---|
| 3,812,841 | 5/1974 | Isaacson | 600/29 |
| 4,934,999 | 6/1990 | Bader | 600/29 |
| 5,004,454 | 4/1991 | Beyar et al. | |
| 5,030,199 | 7/1991 | Barwick et al. | |
| 5,352,182 | 10/1994 | Kalb et al. | 600/30 |
| 5,478,305 | 12/1995 | Craggs | 600/31 |
| 5,509,427 | 4/1996 | Simon et al. | 600/29 |

FOREIGN PATENT DOCUMENTS 0182409  5/1986  European Pat. Off. .

*Primary Examiner*—Linda C. M. Dvorak
*Assistant Examiner*—R. Kearney
*Attorney, Agent, or Firm*—Orum & Roth

[57] ABSTRACT

The present invention relates to a valve (1) intended for positioning in the urethra (2) or similar of a patient in the upper part (2A) of the urethra, which exhibits means for emptying the patient's urine bladder (5) or similar through the valve (1). The valve (1) is so arranged as to be positioned in the urethra (2), etc., and to be withdrawn from it with the help of a tool capable of being accomodated in the urethra, etc., and activated from the outside (10) of the patient's body, and the valve (1) is adjustable from the outside (10) of the patient's body for the purpose of achieving emptying of the urine bladder (5), etc. The primary technical objectives are that the construction must be leakproof, simple to open and close by the patient, tolerated by the body, and free from side-effects. The valve must be adapted to suit the sex, age and body weight of the patient and the size of the urethra.

13 Claims, 4 Drawing Sheets

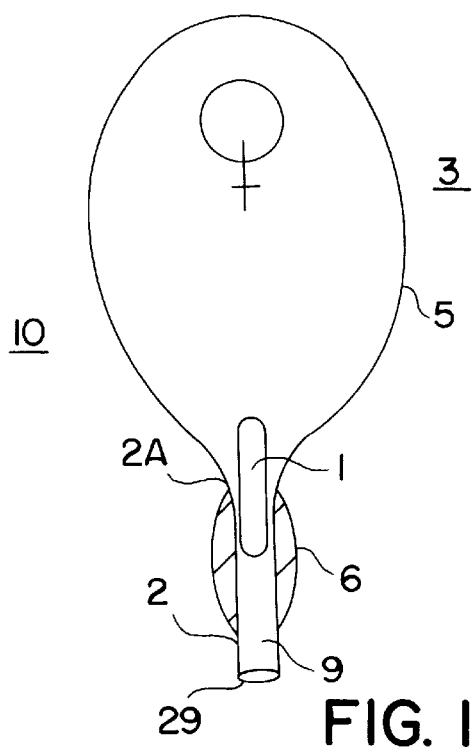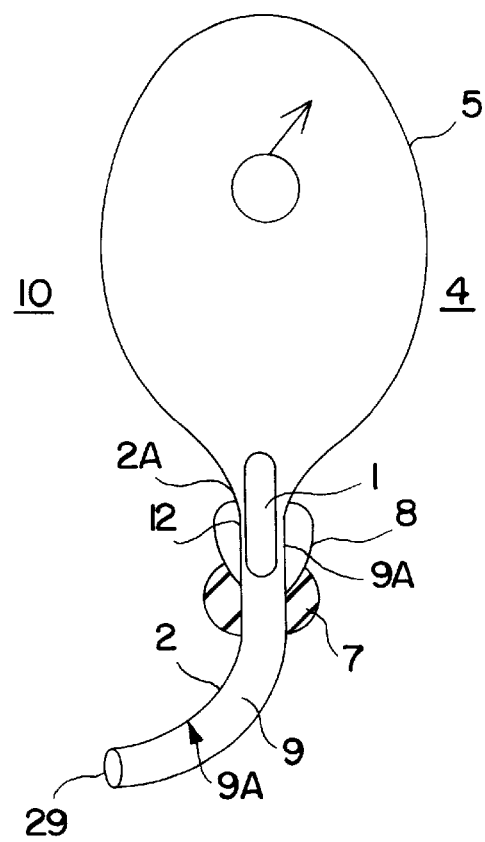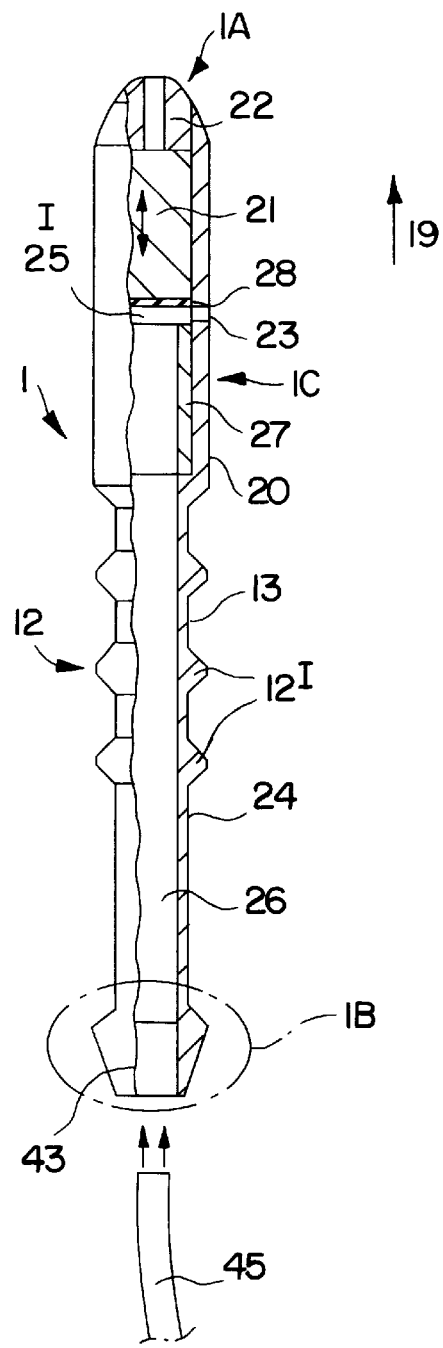
FIG. 1
FIG. 2

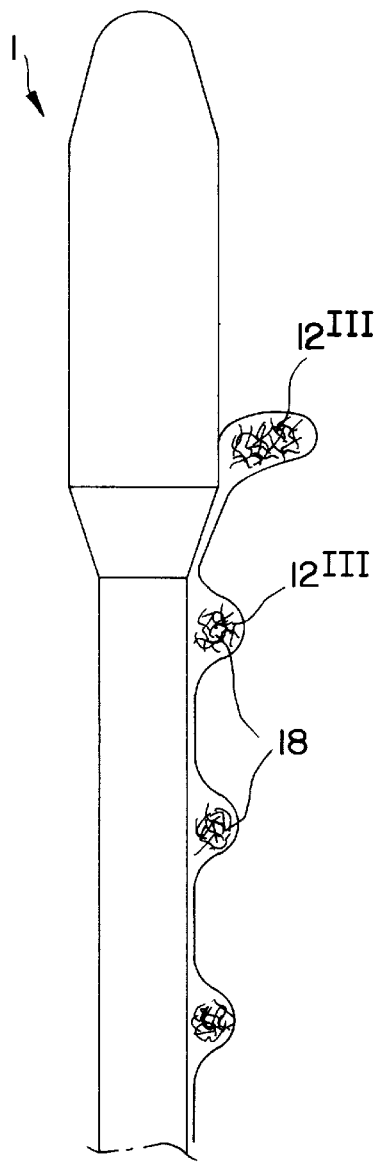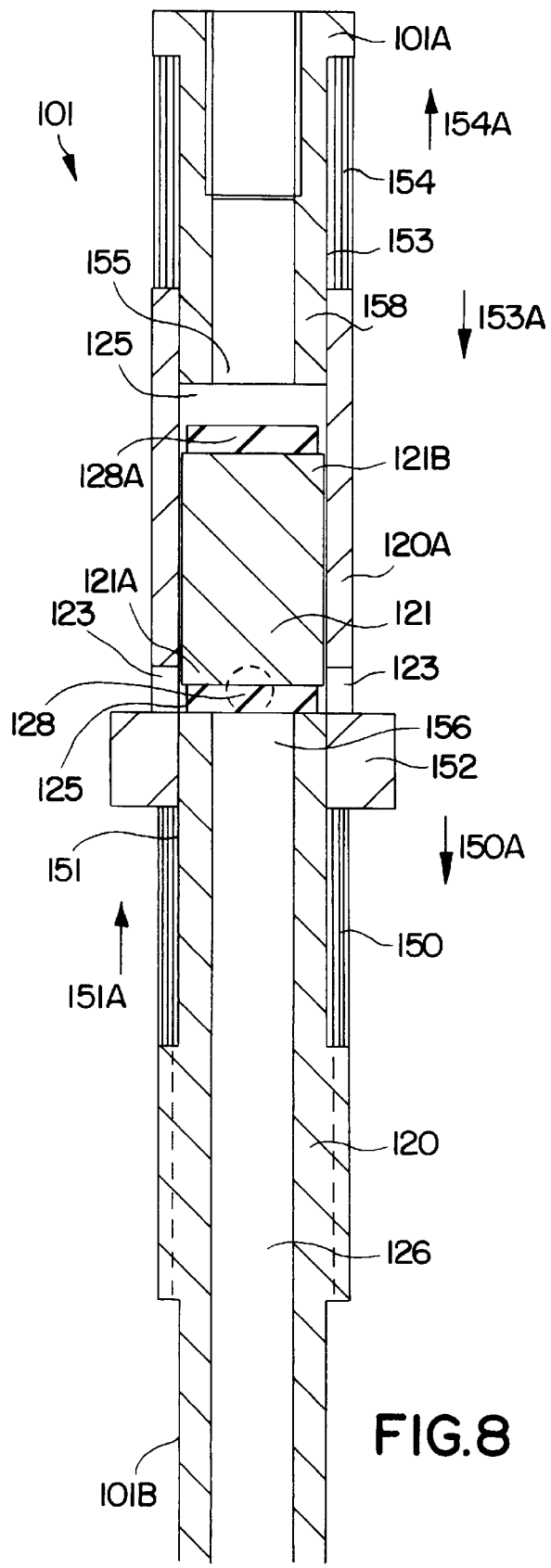
FIG.7
FIG.8

VALVE

The present invention relates to a valve intended for positioning in the urethra or similar of a patient in the upper part of the urethra, which exhibits means for emptying the patient's urine bladder or similar through the valve.

BACKGROUND

Involuntary leakage of urine is a very common disorder. Urinary incontinence is not life-threatening but it has a strong negative influence on Quality of Life.

About 10% of the population, mostly children and elderly people, have an insufficient control of their urinary bladder. The great majority of these have a minor degree of incontinence allowing them to lead a good life with the aid of simple measures such as a small incontinence pad or frequent change of underwear. The rest, about 1% of the population, have a more severe incontinence that poses a serious social problem. Young people who are physically impaired regard the incontinence as a more severe handicap than the inability to walk. The urinary incontinence is considered to be the most serious obstacle for the creation of lasting relationship to other people, for their ability to live an independent, life, and for their adaptation to the society both on the private and the professional level.

The more serious forms of urinary incontinence are caused by congenital malformations of the bladder or the nerves to the bladder (e.g. myelomeningocele), or traffic accidents with injury to the spinal cord, or pelvic floor damage at child birth, or infections of the nervous system (such as encephalitis or meningitis). Furthermore, several of the diseases of old age, such as prostatic hyperplasia of Parkinson's disease, may cause urinary incontinence.

Generally, urinary incontinence is caused either by involuntary contractions of the bladder muscle (so called unstable bladder), or by insufficient contraction of the urethral sphincter muscle. Unstable bladder can be treated with medication or bladder training with good results. The situation is more problematic when the incontinence is due to a weak or damaged sphincter muscle. So far, there is no medication available that can increase the contraction of the sphincter without giving at the same time unacceptable side effects. The only efficient treatment today for severe cases is operation whereby an artificial sphincter is implanted around the bladder neck or urethra, controlled by the patient via an implanted pump system. This is major surgery, the cost is high (in Sweden at least SEK 100 000), the operation is unsuccessful in 15–25% of patients, and the device has a limited life span, meaning that reoperations will have to be performed in order to exchange components that have broken down. Therefore, many patients choose to keep their severe incontinence instead of going through a major operation with uncertain prospects.

Less than $\frac{1}{1000}$ of the population have urinary incontinence due to a faulty sphincter muscle, the most severe and therapy-resistant form of incontinence. Still, this kind of incontinence is found in millions of patients on a global scale.

Since many years, the medical profession has been searching for alternative ways to treat patients with an incompetent sphincter muscle. Some center (München, San Francisco) try esoteric and costly methods, such as transplantation of muscle or implantation of electrostimulators. Plugs or valves have been developed (e.g., U.S. Pat. Nos. 4,679,546 and 4,643,169) for implantation in the urethra, but previously used methods and materials have caused urinary stone and infection, so these devices have been abandoned. However, the development of biocompatible materials during recent years has improved the chances for prolonged survival of an artificial valve within the urinary tract.

Therefore, the main purpose of the present invention is to develop a valve for placement in the urethra or any other emptying tube channel in humans or animals and to construct the valve so that it is well tolerated by the patient's urethra.

The valve is intended to be changed regularly, for instance every 6 months, in order to prevent the development of urinary stone and infection. Furthermore, the pressure within the device keeping the valve in adequate position within the urethra is calibrated so that the valve is well tolerated by the mucous membrane of the urethra but at the same time allowing the entire device to be expelled out of the patient's body in case the bladder pressure would rise to dangerous levels if the opening of the valve would be impaired, thus enhancing the safety of the valve.

Said object is achieved by means of a valve in accordance with the present invention, which is characterized essentially in that a valve body accommodated internally within a valve housing is formed by a permanent magnet, in conjunction with which a stop is situated at the inward-facing part of the valve housing, and in that drainage holes extend to the area of the central part of the valve housing and the central channel of the valve housing to permit urine to be emptied through the valve in its inserted position, and to seal the valve with the valve body in its extended position, and it that the valve is so arranged as to be positioned in the urethra, etc., and to be withdrawn from it with the help of a tool capable of being accommodated in the urethra and activated from the outside of the patient's body, in that the valve is retained in the urethra by means of holding devices with a sealing and retaining effect around the periphery of the valve, which devices are formed from self-expanding bodies, and in that the valve is adjustable from the outside of the patient's body for the purpose of achieving emptying of the urine bladder, etc.

The invention is described below as a number of preferred illustrative embodiments with reference to the accompanying drawings, in which FIG. 1 illustrates schematically the position of the valve respectively in a woman and in a man;

FIG. 2 shows a partially sectioned view of a valve activated to the open position;

FIG. 7 shows a sectioned view of a further variant of a valve with retaining bodies for same;

FIG. 8 shows a second prototype of a valve which exhibits a valve body so arranged as to be capable of activation with electrical impulses.

Figure 3:
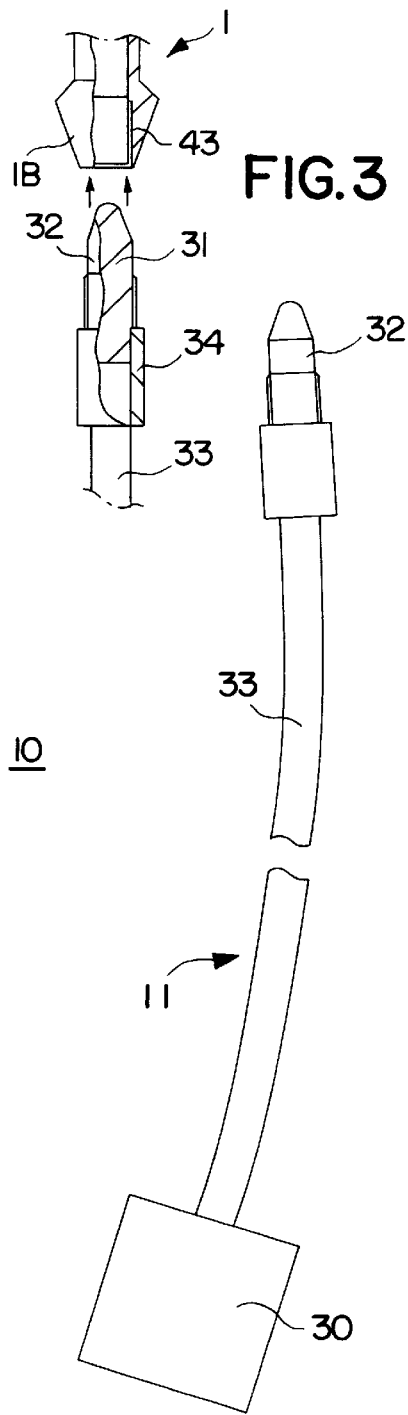
FIG. 3 shows application and removal aids for the valve.
Figure 4:
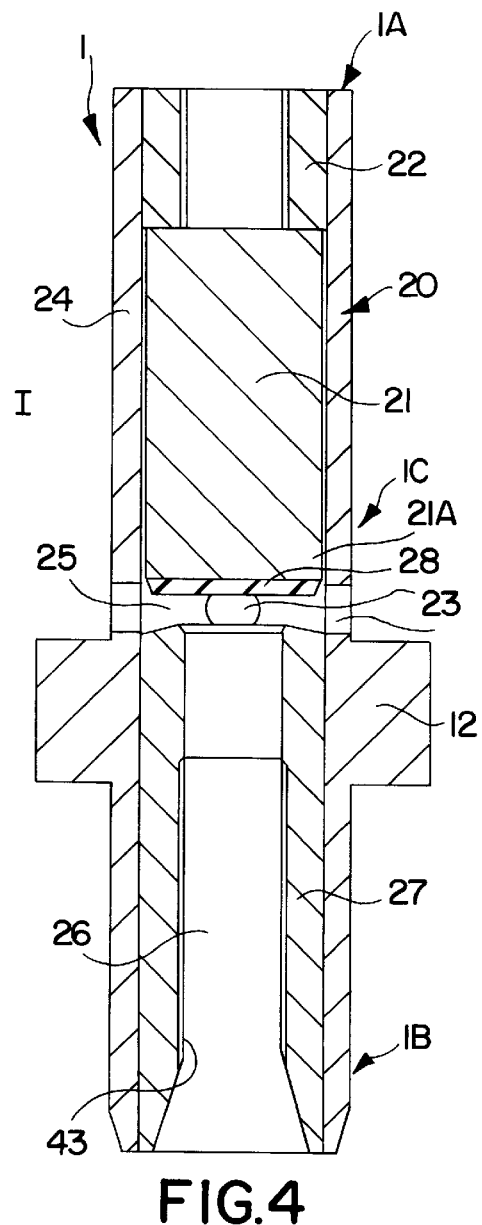
FIG. 4 shows a sectioned view of a first prototype of a valve exhibiting a manually activated valve body.

A valve 1 in accordance with the present invention, which is so arranged as to be positioned in an intended position in the urethra 2 or in some other duct intended for emptying in a patient, either female 3 or male 4, at the upper part 2A of the urethra, etc., in conjunction with the urine bladder 5 on the inner side of the sphincter muscle 6 of the urethra in the case of females, and the sphincter muscle 7 and prostate 8 in the case of males, and which exhibits means for emptying the patient's urine bladder 5 or some other internal body cavity intended for emptying, through the valve 1, is so arranged as to be positioned simply and without pain in the urethra 2, etc., and to be regulated externally by the patient.

More specifically, the entire valve 1 is so arranged as to be capable of being positioned in the urethra 2, etc., in its internal space 9, and of being removed from it with the help of a tool 11 intended for that purpose capable of being accomodated inside the urethra 2, etc., and activated from the outside 10 of the patient's body. The valve 1 in accordance with the invention is also adjustable from the outside 10 of the patient's body to permit emptying of the urine bladder 5, etc.

Said valve 1 is retained in the urethra 2 at its inner part 2A by holding devices 12 exerting both a sealing and retaining effect around the periphery of the valve.

Said holding devices 12 can be formed by thickened parts 12$^I$ of the valve 1 at its rear end 1B around its outer surface 13.

Holding devices can also be formed from laterally extending bodies 12$^{II}$, preferably capable of being filled with a liquid 17, for example a liquid that is harmless to the patient in the event of it being able to leak into the urethra 2, as may occur when the valve 1 is being withdrawn.

Figure 5:
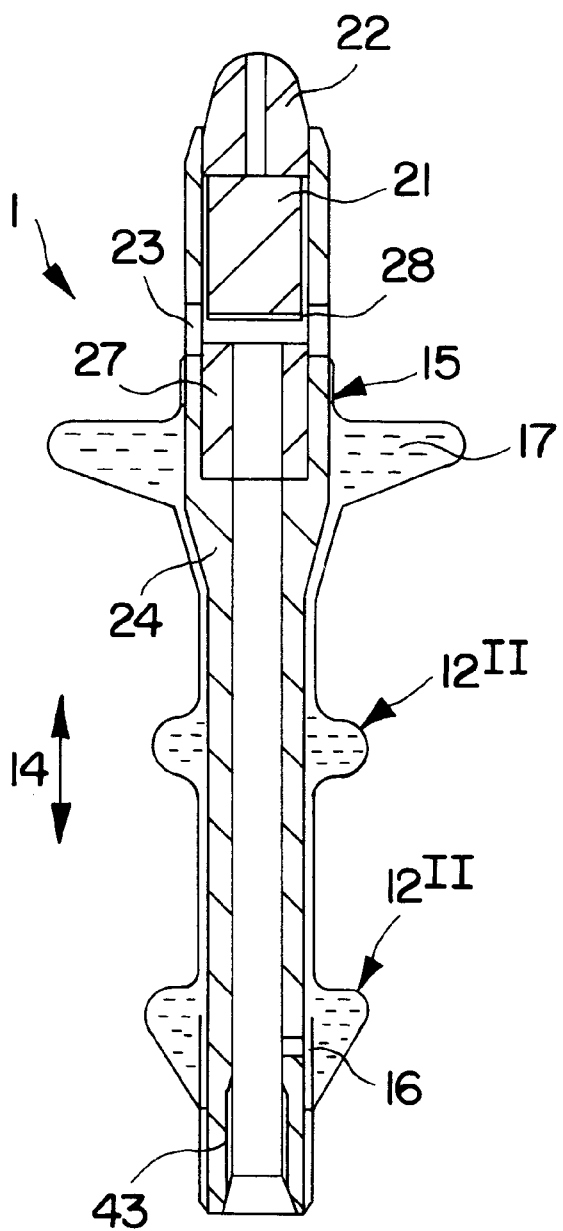
FIG. 5 shows a sectioned view of such a valve adapted for application in the urethra of a patient.
Figure 6:
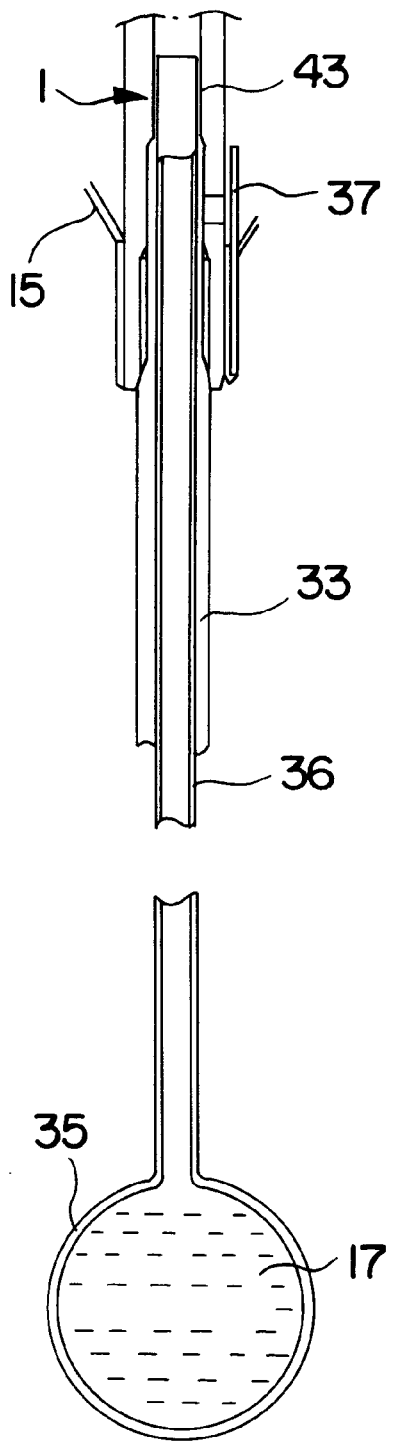
FIG. 6 shows an aid for applying the valve.

Illustrated in FIG. 5 is an embodiment of a valve 1 in which a number of annular bodies 12$^{II}$ distributed along the longitudinal extent 14 of the valve, which bodies are formed by a common rubber balloon 15 with a common filling orifice 16 for the filling liquid 17, attached to the valve 1 around its ends with adhesive, form the aforementioned devices for holding and sealing the valve 1 against the inner surface 9A of the internal cavity 9 of the urethra. None of the cited patents show a valve where, in an axial direction, a movable permanent magnet valve body closes a radially disposed opening the valve housing.

Illustrated in FIG. 7 is an embodiment in which such holding devices 12$^{III}$ are formed by rolls 18 of a compressible material, which rolls are applied externally around a valve 1 of the kind intended here, for example in the form of a rubber material. Said rolls 18 may be of a kind such that they swell as they come into contact with liquid, so as to achieve the effective sealing and retention of the valve in the urethra.

The valve 1 may, as shown in drawings such as FIGS. 1–7, be of a mechanical kind with a valve body 21 accommodated in such a way as to be capable of movement inside a cylindrical valve housing 20, which valve body preferably consists of a permanent magnet, in conjunction with which a stop 22 is situated in the inward-facing part 1A of the valve housing, and thus the valve, i.e. that part of the valve 1 that is intended to face towards and to be inserted in the urethra 2.

Also present is a number of drainage holes 23 extending preferably perpendicularly through the valve 1. Said drainage holes 23 extend through the tubular outer casing 24 of the valve as far as an internal cavity 25 in the central part 1C of the valve housing and the transcurrent axial central channel 26 of the valve housing, for the purpose of emptying urine, etc., through the valve 1 with the valve body 21 pushed into its inserted position I, and of connecting the valve 1 to said valve body 21 when it is in its extended position, in which it is retained by the effect of the magnet, and the connected drainage holes 23 and central channel 26, thereby preventing the escape of urine through the valve 1.

A valve seat 27 is accommodated internally in the valve housing 24 and interacts with the outward-facing end 21A, preferably in the form of a permanent magnet, of the valve body. The valve seat 27 is constructed preferably as a sleeve together with an appropriate and matching seal 28, for instance attached to the valve body 21, to interact with said valve body 21 between same 21 and at least one valve seat 27.

Said valve 1 is capable of manual actuation. For the purpose of emptying the urine bladder 5, the valve body 21 must be moved mechanically with the help of an actuating device 45, such as a catheter, a probe, a wire, or a C-shaped piece of tubing, capable of being introduced from the outside through the urethra 2 as far as the valve 1 in the direction 19 of the stop 22. The preferably symmetrically arranged drainage holes 23 in the valve body 1 at the base 5A of the urine bladder are opened in this way.

The technical solution provided by the valve has already demonstrated its effectiveness in bench tests. The next step, which is imminent, is to evaluate the prototype in animal experiments.

If the valve described here can be executed in a way that is well tolerated by the body, it will doubtless be acclaimed as an important medical advance. It must be capable of being positioned by a simple cystoscopy procedure, which, in adult patients, does not even require general anaesthesia and should be performed under a local anaesthetic. Given the right surface treatment, the valve should be capable of remaining in place for at least six months, and perhaps longer, before it needs replacement. With the design of the valve described here, removal and insertion of a new valve should also be a simple procedure.

The medical advance lies essentially in the fact that the alternative for that group of patients with a weak urethra sphincter muscle is major surgery, the outcome of which, as already mentioned, is not always satisfactory.

Many patients with a dysfunctional sphincter muscle 6,7 are already being advised to insert a catheter into the urine bladder 5 at regular intervals; this is known as Clean Intermittent Catheterization (CIC). For these individuals, it is sufficient to have a valve 1 with a permanent magnet 21 that is opened by introducing a catheter 45 or a probe into the urethra 2. In most cases, however, it is desirable to have a valve with an electromagnet capable of being opened by transcutaneous induction to a coil positioned in the subcutaneous fat layer, thereby dispensing with the need to introduce a catheter into the urethra. For previously severely incontinent persons, who are able in this way to control their urethra in a totally non-invasive fashion, the valve would represent an enormous increase in their quality of life.

The valve body 21, which, like the valve seat 27, preferably consists of a permanent magnet, is always in the closed position if it is mechanically inactivated externally. This is made possible thanks to the force with which the magnet 21 is pulled against the valve seat 27, which preferably also consists of a permanent magnet.

Said valve 1, which is positioned in the inner upper part 2A of the urethra, can thus be regarded as replacing a damaged or dysfunctional sphincter muscle 6,7 for an urethra 2.

The valve housing 20 and the stop 22 can be made of bronze or titanium, and the valve seat 27 and the valve body 21 can consist of permanent magnets, whilst the seal 28 can consist of a glued-on sheet of silicone rubber of the desired thickness. All components other than the seal 28 are coated with a nickel anti-corrosion treatment, which also serves as the base for subsequent plating with gold, which is inert, is not rejected by the tissues, and does not provide a point of attachment for urine crystals and bacteria. The application of such a valve 1 in the right situation/position in a patient is possible by causing the valve 1 to be introduced through the urethra 2 from its external opening 29 with the help of a combined application/removal tool 11, for example of the kind illustrated in the drawings in FIG. 3. A nipple 31 situated at the front, which can exhibit externally threaded devices 32 that are capable of interacting with internally threaded devices 43 on the rear end part 1B of the valve to permit them to be securely screwed together, forms a guide component and a means of attachment to the valve 1. When the valve 1, after having been securely screwed to the tool 11, has been introduced through the opening 29 of the urethra to the desired extent, which can be verified using ultrasound or x-rays, etc., the nipple 31 is unscrewed with the help of a rear handle 30, for example on a flexible cable 33, and is withdrawn from the urethra 2. A clamping sleeve 34 connects the nipple 31 to the cable 33. Means other than threaded devices for the attachment of insertion tools to the valve are possible, e.g. in the form of a grab claw.

The valve 1 is then retained in position in the urethra 2 with the help of the external holding devices 12 of the valve 1, at the same time as a good seal past the valve 1 is achieved so as to prevent leakage.

The holding devices $12''$ can be filled with liquid 17 from a compressible container 35, which is connected via a filler hose 36 running internally in the flexible insertion cable 33 to the valve 1. A flap valve 37, which communicates with the balloon 15 attached to the valve, permits the supply of the liquid 17 to the different parts $12''$ of the ring. When removing the valve, said parts $12''$ of the ring can be punctured jointly to enable the valve 1 to be pulled out easily by means of the tool 11.

The valve 1, which can be made in different sizes to suit the urethra and the incontinence problem of the individual patient, must be replaced at intervals of approximately six months.

An electrically actuated valve 101, which is illustrated in the drawings in FIG. 8, permits actuation of the valve from outside the patient's body without the need for the introduction through the urethra 2 of any long devices to effect emptying. The valve 101 is so arranged as to be opened or closed by means of electrical impulses through so-called remote control.

Present inside a cylindrical valve housing 120 at the rear end 101B of the valve is an internal axial central passageway 126, and present around said valve seat 120, which is formed by a magnetic core, is a magnetic winding 150, which exerts a pulling force 150A to close the valve 101, and a further magnetic winding 151, which exerts a pushing force 151A in the opposite direction to open the valve 101 in the area of the centre 152 of the valve.

Similarly present at the front end 101A of the valve are magnetic windings 153 and 154, which respectively exert a pushing force 153A and a pulling force 154A for the purpose respectively of closing and opening the valve 101.

A moving valve body 121, which is preferably also in the form of a permanent magnet body of cylindrical form, is accommodated so that it is free to move in a space 125 inside the front valve housing part 120A of the valve 101 and is made of a bronze material or titanium.

A seal 128, 128A is attached to the respective end 121A, 121B of the moving valve body 121 by means of magnetic material, enabling it to close the respective end 155, 156 of the central passageway 126 in the valve seat 120. The material used in the seal is preferably silicone rubber, although consideration can be given to the use of other suitable elastic material.

The valve body 121 is self-retaining in the open/closed position, thanks to the magnetic force, and is so arranged as to be opened/closed by means of an electrical impulse. The electrical impulse reverses the polarity of the seat 120 and a stop 158 inside the front part 101A of the valve, in relation to the valve body 121. Drainage holes 123 also lead through the part 120A of the valve housing to the internal cavity 125 beneath the valve body 121 for connection to the passageway 126.

When the valve 101 is positioned in the upper part of an urethra, said drainage holes 123 are situated inside the actual urine bladder, in the vicinity of its base, whereas the external attachment parts 152, etc., of the valve are attached to the urethra on its inside. The attachment devices 152 are appropriately of a similar kind, as described in the preceding embodiment.

For approximately one ms during polarity reversal, a small pushing force acts on the part (either the seat or the stop) against which the valve body is in contact, and a stronger pulling force acts on the opposite end of the valve body. The valve body can also be opened mechanically independently of the closing impulses.

The permanent magnets are preferably in equilibrium, so that a relatively small polarity reversal impulse, as described above, causes the valve body respectively to open and close the valve.

Said valve also has attachment devices so arranged as to be filled with a suitable fluid at a pressure tolerable by the patient's mucous membranes. The valve, which is intended to be replaced at regular intervals, for example every sixth month, by external influence, is so arranged as to be capable of being ejected automatically from the urethra, etc., if excessive pressure builds up inside the urine bladder, etc., for example is the valve opening process is impeded. There is accordingly no security risk, thanks to the safety function whereby the valve is able to leave the patient's body, which function is effective independently of the valve function.

Electrical valve

The electrical valve must satisfy the above criteria, apart from the possibility that insertion/removal of the electrical control means of the valve may require a minor surgical operation.

The invention is not restricted to the illustrative embodiments described above and illustrated in the drawings, but may be modified within the scope of the Patent Claims without departing from the idea of invention.

What is claimed is:

1. A valve adapted to be positionable into an upper part of a urethra, said valve for emptying a patient's urine collected within his bladder, comprising: a tubular valve housing having an upper, lower, and central part and a central channel therein; a valve body formed by a permanent magnet accomodated with the upper portion of the valve; a stop situated at the upper part of the valve housing; a valve seat situated below said valve body, said central part having a plurality of drainage holes extending perpendicularly through said tubular housing, said drainage holes located in the area between the stop and the valve seat, said central channel of the valve housing in communication with said drainage holes, said central channel and said drainage holes emptying urine through the valve while in an inserted position, and sealing the valve with the valve body in its extended position, the valve arrangeable so as to be positionable within the urethra and withdrawable from it with the help of a tool capable of accommodation in the urethra, said valve arranged and constructed to accommodate a manual activator introducible from the outside of the patient's body through the urethra up to the valve; a plurality of holding devices securing the valve in the urethra producing a sealing and retaining effect around a periphery of the valve, said devices formed from a plurality of self-expanding bodies, the valve adjustable from the outside of the patient's body for emptying of the urine bladder, and said valve seat accommodated internally in the valve housing and interactive with the outward-facing end of the valve body in the closed position.

2. The valve of claim 1, wherein the holding devices are adopted to be filled with a liquid.

3. The valve of claim 2, wherein said holding devices are formed by a common rubber balloon having a common filling orifice for filling said liquid therein.

4. The valve of claim 2, wherein said valve is so arranged as to be opened and/or closed by means of electrical impulses through a remote control.

5. The valve of with claim 3, wherein said valve is so arranged as to be opened and/or closed by means of electrical impulses through a remote control.

6. The valve of claim 1, wherein said holding devices are formed by a compressible material.

7. The valve of with claim 6, wherein said valve is so arranged as to be opened and/or closed by means of electrical impulses through a remote control.

8. The valve of claim 6, wherein the valve seat is constructed as a sleeve, and a seal is provided to interact with the valve body between the valve body and said valve seat.

9. The valve of claim 8, wherein said valve is so arranged as to be opened and/or closed by means of electrical impulses through a remote control.

10. Valve in accordance with claim 1, characterized in that the valve (101) is so arranged as to be opened and/or closed by means of electrical impulses through so-called remote control.

11. The valve of claim 1, wherein said holding devices are fillable with a suitable fluid at a pressure tolerable by the patient's mucous membranes, and wherein the valve replaceable at regular intervals, arrangeable so as to be capable of automatic ejection from the urethra due to a pressure differential building up.

12. The valve of with claim 1, wherein said valve is so arranged as to be opened and/or closed by means of electrical impulses through a remote control.

13. A valve for implantation within the urethra of a body of a patient at the juncture of the urethra and the bladder, for controlling the flow of urine through the urethra, comprising:

an axially elongated hollow tubular housing of substantially cylindrical configuration having an internal cavity, an upper and inward-facing end, a lower and outward-facing end, and a central part therebetween, said central part including a plurality of radially arranged drainage holes for communicating urine from said bladder, through said holes, and into said internal cavity;

a valve stop inserted within said upper end;

a movable valve body disposed at said upper end of said tubular housing formed by a permanent magnet and disposed within said housing below and stop;

a valve seat disposed within said housing, below said drainage holes, said valve body movable between said seat and said stop, wherein when said valve body is in resting contact against said seat, said drainage holes are closed, said seat formed by a permanent magnet and having an axially disposed central channel in communication with said cavity of said housing, a lower end of said seat having an upwardly converging throat for removably coupling an insertion and removal instrument therewith;

a plurality of holding devices in the form of self-expending bodies located on an exterior of said housing at axially spaced locations generally between said seat and said lower end, wherein said permanent magnets of said valve body and seat are selectively balanced so as to create a near equilibrium condition of magnetic attraction between said seat and valve body where said valve body is magnetically attracted downwardly against said seat with a deminimus attraction force, thereby closing said drainage holes, wherein direct manipulation against said valve body with one of a wire, catheter and probe from outside said body causes said valve body to readily overcome said balanced magnetic attraction force so as to unseat and open, thereby allowing passage of urine from said bladder and into said drainage holes of said valve.

* * * * *